United States Patent [19]

Bulten et al.

[11] 4,044,035

[45] Aug. 23, 1977

[54] METHOD FOR THE PREPARATION OF ALKYL TIN HALIDES

[75] Inventors: Eric J. Bulten, Bilthoven; Francois Verbeek, Harmelen, both of Netherlands

[73] Assignee: Commer S.r.l., Lodi (Mi), Italy

[21] Appl. No.: 670,823

[22] Filed: Mar. 26, 1976

[30] Foreign Application Priority Data

Apr. 4, 1975    Netherlands ........................ 7504073

[51] Int. Cl.² ............................................... C07F 7/22
[52] U.S. Cl. .................................................. 260/429.7
[58] Field of Search ...................................... 260/429.7

[56] References Cited

U.S. PATENT DOCUMENTS

| | | | |
|---|---|---|---|
| 3,340,283 | 9/1967 | Glaskey | 260/429.7 |
| 3,400,141 | 9/1968 | Hoye et al. | 260/429.7 |
| 3,414,595 | 12/1968 | Oakes | 260/429.7 |
| 3,475,472 | 10/1969 | Suzuki et al. | 260/429.7 |
| 3,745,183 | 7/1973 | Katsumura et al. | 260/429.7 |
| 3,824,264 | 7/1974 | Bulten | 260/429.7 |

*Primary Examiner*—Helen M. S. Sneed
*Attorney, Agent, or Firm*—Spencer & Kaye

[57] ABSTRACT

The preparation of alkyl tin halides is carried out by direct conversion of a gaseous lower aliphatic halide with a stannous halide in the presence of a nitrogenous solvent of the acid amide type at substantially atmospheric pressure. The acid amide solvent is present in quantities of approximately 1-4 mol per mol stannous halide. This reaction proceeds without the production of any trialkyl tin compounds as by-products.

5 Claims, No Drawings

METHOD FOR THE PREPARATION OF ALKYL TIN HALIDES

BACKGROUND OF THE INVENTION

The invention relates to the preparation of alkyl tin halides by means of direct conversion of an aliphatic halide with a stannous halide in the presence of a nitrogenous compound and of iodine and/or a iodide as a catalyst.

According to prior art two types of direct synthesis reactions are known:

a. reaction of metallic tin with an alkyl halide under the influence of a catalyst, this reaction, for which in the (patent) literature a great variety of catalysts has been described, leads to the formation of dialkyl tin halides as main product, together with trialkyl and/or mono alkyl tin halides as by-product(s)

b. reaction of a stannous halide with an alkyl halide under the influence of a catalyst.

For this reaction (b), which according to the literature leads to the formation of mono alkyl tin halides, also a number a catalysts has been described in the (patent) literature, such as, for instance, with compounds of bivalent sulphur and/or selenium, or also with amines as catalysts (in quantities of 0.01 – 2% by weight), whether or not combined with the addition of slight amounts of iodide and/or inorganic iodides.

These reactions are in particular carried out in an autoclave upon application of the low boiling methyl, propyl and butyl halides and then require a heating time of many hours.

SUMMARY OF THE INVENTION

Now it was found that the reaction of a stannous halide with a lower alkyl halide leads to the formation of dialkyl tin halides, if the reaction is carried out by introduction at substantially atmospheric pressure of a gaseous, lower alkyl halide in the reaction mixture in the presence of a solvent the acid amide type in quantities of approximately 1-4 mol per mol stannous halide.

Moreover, it appeared that in particular when this reaction was applied to methyl halides, exclusively dimethyl tin dihalide is formed without a trace of the corresponding monomethyl or trimethyl compound.

It is observed that in a copending U.S. Patent application Ser. No. 634,255 of the same assignee similar reaction conditions are described for the reaction of alkyl halides with metallic tin.

DETAILED DESCRIPTION OF THE INVENTION

Dialkyl tin dihalides form the basic products for the preparation of the commercially important dialkyl tin stabilizers for polyvinyl chloride. Upon application of these stabilizers in polyvinyl chloride used for packaging foodstuffs, viz. dimethyl and dioctyl tin stabilizers, in many countries it has been decreed that these products must not contain the corresponding triorgano tin compounds or are allowed to contain only minimum amounts of them. For, in general, triorgano tin compounds are considerably more toxic to warmblooded beings than the diorgano tin compounds.

Consequently, an important technical advantage of the present process concerns the total absence of trialkyl tin compounds in the reaction product, in particular in preparing dimethyl tin dihalides.

The reaction can also be carried out at atmospheric pressure with the low-boiling alkyl halides if the gaseous halide is introduced into a reaction vessel that is sealed with a mercury seal.

Of the three qualifying lower alkyl halides RI, RBr, RCl, preferably, the cheaper chloride is used. For reasons of economy, moreover, stannous chloride $SnCl_2$ is preferred; it can also be done, however, with $SnBr_2$, $SnI_2$.

The liquid acid amide is used in a ratio of 1-4 mol per mol $SnX_2$, preferably 1.5-2.5 mol acid amide per mol $SnX_2$. The temperature applied is between 100° C and 200° C, preferably 130°-160° C.

Of the solvents of the acid amide type in particular methyl or ethyl substituted derivatives are of importance, such as dimethyl formamide, methyl formamide, ethyl formamide, methyl and dimethyl acetamides, methyl and dimethyl propionic acid amides and, furthermore, whether or not substituted phosphoric acid amides, such as, for instance, hexa butyl phosphoric acid triamide and more particularly hexamethyl phosphoric acid triamide (HMPT).

The iodine-catalyst is added as NaI, or an other suitable inorganic iodide or in the form of some crystals of iodide, in quantities of 0.01-0.5 mol per mol stannous halide, preferably of 0.05-0.2 mol per mol stannous halide.

For the analysis of the reaction mixture, with advantage use can be made of thin-layer chromatography, gas chromatography and also nuclear magnetic resonance/-spectroscopy.

The further processing of the reaction mixture obtained can be effected according to methods known per se, for instance, extraction, distillation, and the like.

Besides the only organic reaction product, viz. the dialkyl tin dihalide, in the reaction mixture as by-product the corresponding inorganic stannic halide can be found. Winning this by-product can be of advantage, since it concerns here an important commercial product for innumerable industrial processes. If desired, it can be converted again via the reaction known per se with tin into a corresponding stannous halide and as such be recirculated again.

COMPARATIVE EXAMPLES

EXAMPLE I

In a reaction vessel provided with a reflux condensor and stirrer the following mixture was brought:

9.5 gs. (0.05 mol) of stannous chloride ($SnCl_2$)

10 mls. (0.055 mol) of hexamethyl phosphoric acid triamide (HMPT)

1.5 gs. (0.01 mol) of sodium iodide.

Via a gas inlet tube the air in the reaction vessel was replaced by an atmosphere of methylchloride gas, a constant methyl chloride pressure of approximately 3 cms. of mercury being maintained by means of a mercury seal, connected with the discharge opening of the reflux condensor.

As a result of the heat of solution of methyl chloride in the reaction mixture the temperature rose to 40° C. While the mixture was vigorously stirred, it was heated at 140°-150° C, a constantly takeup of methylchloride that went through the solution, being effected. Totally, substantially 5 gs. (0.1 mol) of $CH_3Cl$ were absorbed.

After 3 hours at 140°-150° C the reaction mixture was taken up at ambient temperature in 50 mls. of methanol. The HMPT complexes of inorganic tin chlorides insoluble in methanol were isolated by filtration. The methanol filtrate was analysed with the aid of Nuclear Magnetic Resonance/spectroscopy (NMR), a weighed out quantity of Me₄Ge being used as internal standard. The analysis showed that the net output of the conversion of inorganic stannous chloride into dimethyl tin dichloride amounted to 60%, whereas no methyl tin chloride, trimethyl tin chloride or tetramethyl tin could be shown.

EXAMPLE II

In the same way as described in example I an experiment was carried out with methyl bromide gas (instead of methyl chloride gas). In the process, initially 14.0 gs. (0.05 mol) of $SnBr_2$, 10 mls. of HMPT and 1.5 gs. of NaI were used. The net output of dimethyl tin dibromide amounted to 63%. Other methyl tin compounds could not be shown.

EXAMPLE III

In the same way as described in example I an experiment was carried out with 20 mls. (0.11 mol) of HMPT. After 6 hours at 140°–150° C it was found that the net output of dimethyl tin dichloride amounted to 89%. Tetramethyl tin, trimethyl tin chloride and methyl tin trichloride could not be shown.

EXAMPLE IV

In the same way as described in example I an experiment was carried out with 0.05 mol (14 gs.) of stannous bromide (instead of with stannous chloride), 10 mls. of HMPT and 1.5 gs. NaI. The net output of dimethyl tin chloride bromide amounted to 70%.

EXAMPLE V

In the same way as described in example I, was operated with methyl chloride, but now instead of the 10 mls. of HMPT successively were used besides 9.5 gs. of $SnCl_2$ and 1.5 gs. of NaI, 10 mls. of dimethyl acetamide
10 mls. of dimethyl formamide
10 mls. of methyl formamide.

In these experiments a conversion of more than 70% into the dimethyl tin dichloride was obtained.

In these reaction mixtures either, there could not be shown any presence of trimethyl tin chloride or methyltin chloride besides the dimethyl tin dichloride desired.

We claim:

1. A method for preparing an alkyltin halide by direct conversion of a stannous halide with an alkyl halide at raised temperatures in the presence of iodine and/or iodide as a catalyst, to obtain a dialkyl tin dihalide, comprising:

forming a mixture of said stannous halide, said catalyst, and an acid amide solvent, said acid amide solvent being present in an amount of about 1 to 4 mols per mol of said stannous halide; and introducing, at substantially atmospheric pressure, a gaseous, lower alkyl halide into the mixture to bring about reaction of said stannous halide with said lower alkyl halide.

2. A method according to claim 1, wherein one of the methyl halides, $CH_3Cl$, $CH_3Br$, or $CH_3I$, is used as an alkyl halide.

3. A method according to claim 1, wherein the acid amide solvent is used in an amount of 1.5 to 2.5 mols per mol stannous halide.

4. A method according to claim 1, wherein hexamethyl phosphoric acid triamide is used as an acid amide solvent.

5. A method according to claim 1, wherein the acid amide is dimethyl formamide, methyl formamide, ethyl formamide, methyl acetamide, dimethyl acetamide, methyl propionic acid amide, dimethyl propionic acid amide, hexa butyl phosphoric acid triamide, or hexamethyl phosphoric acid triamide.

* * * * *